United States Patent [19]
Samejima et al.

[11] 4,389,331
[45] Jun. 21, 1983

[54] PROCESS FOR PREPARING PHARMACEUTICALLY ACTIVE COMPOUND-CONTAINING MICROCAPSULES

[75] Inventors: Masayoshi Samejima, Minoh; Goichi Hirata, Yawata; Yoshiyuki Koida, Katano, all of Japan

[73] Assignee: Tanabe Seiyaku Co., Ltd., Osaka, Japan

[21] Appl. No.: 194,809

[22] Filed: Oct. 7, 1980

[30] Foreign Application Priority Data

Oct. 31, 1979 [JP] Japan ................... 54-141826

[51] Int. Cl.³ .................... B01J 13/02; A61K 9/50
[52] U.S. Cl. ................................. 427/213.3; 424/35
[58] Field of Search ................... 252/316; 424/35

[56] References Cited

U.S. PATENT DOCUMENTS 3,155,590 11/1964 Miller et al. ............... 252/316 X
3,242,051 3/1966 Hiestand et al. ............ 424/33 X
3,531,418 9/1970 Fanger et al. ............... 252/316

FOREIGN PATENT DOCUMENTS 42-528 1/1967 Japan.
44-11399 5/1969 Japan.
50-30136 9/1975 Japan.

Primary Examiner—Richard D. Lovering
Attorney, Agent, or Firm—Jordan B. Bierman; Linda Bierman

[57] ABSTRACT

A process for preparing ethylcellulose microcapsules of a pharmaceutically active compound by phase separation-coacervation of the ethylcellulose is disclosed. In this process, phospholipids are used as a phase-separation-inducing agent.

7 Claims, No Drawings

PROCESS FOR PREPARING PHARMACEUTICALLY ACTIVE COMPOUND-CONTAINING MICROCAPSULES

This invention relates to a process for preparing pharmaceutically active compound-containing microcapsules.

It is known that ethylcellulose microcapsules of a pharmaceutically active compound are prepared by taking advantage of the liquid-liquid phase separation of ethylcellulose in cyclohexane. For example, Japanese Patent Publication (examined) Nos. 528/1967, 11399/1969 and 30136/1975 disclose that butyl rubber, polybutadiene, polyethylene and polyisobutylene are used as the phase-separation-inducing agent; and that said microcapsules are obtained by preparing a hot solution in cyclohexane of ethylcellulose and said phase-separation-inducing agent, dispersing the particles of a medicament in the solution, cooling the dispersion under stirring until the ethylcellulose separate out from the solution to form a liquid phase depositing on and around the particles of the medicament, and then recovering the so formed capsules therefrom. However, these known methods are still unsatisfactory in that cyclohexane used as the solvent during the encapsulation step remains entrapped in the microcapsules, and it is difficult to remove such solvent therefrom even by drying in vacuo under heating. Moreover, when butyl rubber, polybutadiene and polyisobutylene are used as the phase-separation-inducing agent, the removal of said agent from the microcapsules obtained can be effected only by washing the microcapsules with the large excess (e.g., 50 ml/g) of cyclohexane for a long time because of their high adhesiveness and slow velocity of dissolution in the solvent. Additionally, in making such microcapsules, as long as 4 to 10 hours are required to dissolve only one gram of butyl rubber, polybutadiene or polyisobutylene in 30 ml of cyclohexane at 78° C. This inevitably impairs the operational efficiency in making the microcapsules. On the other hand, if polyethylene is used as the phase-separation-inducing agent, said polyethylene is separated as minute particles during cooling the dispersion and deposited on and in the wall of the microcapsules. Since such minute particles of polyethylene can not be washed out completely with a poor solvent such as cyclohexane, therefore, polyethylene is not suitable for use as the phase-separation-inducing agent in making microcapsules having a particle size of less than 100μ.

As an alternative to the above-mentioned methods, U.S. Pat. No. 3,531,418 discloses a method of preparing ethylcellulose microcapsules of a pharmaceutically active compound without using a phase-separation-inducing agent, i.e., by direct flocculation of ethylcellulose induced by change of temperature. However, the ethylcellulose gel depositing on the core material (particles of a pharmaceutically active compound) by this flocculation is not visco-elastic enough to form continuous film on the surface of the core material and is still premature to give the desired coating properties such as impermeability, flexibility, stability and so forth. Moreover, since the coating walls of the microcapsules obtained by this method becomes highly adhesive at around 50° to 65° C. by absorbing cyclohexane or they are liable to agglomerate together into small visible lumps each containing a myriad of individual capsules, it is difficult to obtain free-flowing microcapsules having uniform particle size. Further, said microcapsules can not be tableted without deterioration in the quality of compressed tablets because of the high adhesiveness of the coating walls thereof.

As a result of various investigations, we have now found that the wall characteristics of ethylcellulose film to be deposited on particles of a pharmaceutically active compound can be remarkably improved and the free-flowing microcapsules having uniform particle size can be readily obtained by effecting the phase separation-coacervation of the ethylcellulose in the presence of phospholipids.

According to the present invention, the ethylcellulose microcapsules of a pharmaceutically active compound are prepared by dissolving ethylcellulose and phospholipids in cyclohexane, dispersing particles of a pharmaceutically active compound in said solution, cooling the dispersion under continuous stirring until ethylcellulose separates out from the dispersion to form coating walls on and around the particles of said pharmaceutically active compound, and then recovering the resultant microcapsules therefrom.

Any one of natural and synthetic phospholipids which are soluble in cyclohexane can be used as the phase-separation-inducing agent of the present invention. Suitable examples of said phospholipids include soybean phospholipids, egg-yolk phospholipids, phosphatidyl choline, phosphatidyl ethanolamine, phosphatidyl serine, inositol phosphatide and the like. On the other hand, ethylcellulose having an ethoxy content of about 47.0 to about 51.0 w/w % is preferably used as the wall-forming material of the invention. It is also preferred that the viscocity of said ethylcellulose when measured at 25° C. with respect to a 5 w/w % solution of it in toluene-ethanol (4:1) is within the range of about 10 to about 350 cps, especially 80 to 110 cps. Moreover, any one of pharmaceutically active compounds (or medicaments) which are insoluble or incompatible in cyclohexane or a cyclohexane solution containing either one or both of the phospholipids and ethylcellulose can be used as the core material to be microencapsulated in the present invention. Such pharmaceutically active compound or medicament to be microencapsulated may be either solid, gel or semi-solid. In order to prepare a homogeneous dispersion at the microencapsulation step, it is preferred that said pharmaceutically active compound or medicament has a particlle size of not more than about 1000μ, especially 74 to 500μ. Eligible for microencapsulation as solids are particles of material such as, for example: vitamines (e.g., ascorbic acid), anti-microbial agents (e.g., benzylpenicillin potassium salt, sulfamethomidine), anti-tumor agents (e.g., 5-fluorouracil, bleomycin hydrochloride), metabolic agents (e.g., glutathione), cardiovascular agents (e.g., 2,3-dihydro-2-(p-methoxyphenyl)-5-(2-dimethylaminoethyl)-1,5-benzothiazepin-4-one hydrochloride), analgesics (e.g., acetylsalicylic acid), anti-histaminics (e.g., diphenhydramine hydrochloride), neuro-psycotropic agents (e.g., clacium N-(γ,γ-dihydroxy-β,β-dimethylbutyryl)-γ-aminobutyrate), agents affecting digestive organs (e.g., methylmethionine sulfonium chloride, di-(2-thienyl)-(N-methyl-5-methoxy-3-piperidilidene)methane methylbromixe, precipitated calcium carbonate, 1-(3,4,5-trimethoxybenzoyloxy)-2-dimethylamine-2-phenylbutane maleate), agents affecting respiratory organs (e.g., 1-(3,4,5-trimethoxybenzyl)-6,7-dihydroxy-1,2,3,4-tetrahydroisoquinoline hydrochloride), and so forth. Also eligible for microencapsulation as semi-solids are, for example, ointments such as an ointment composed of 50 w/w % of polyethyleneglycol 4000, 40 w/w % of polyethylene 400 and 10 w/w % of 5-fluorouracil). And pharmaceutically active compounds in the form of "gel" which can be microencapsulated include, for example, dextran gel having a medicament (e.g., methylmethionine sulfonium chloride) adsorbed therein, formaline-treated gelatin gel having dispersed a medicament (e.g., sulfamethomidine) therein, and so forth.

Suitable amount of the phospholipids to be used may vary depending on the amount of each one of ethylcellulose and the pharmaceutically active compound as well as the quantitative ratio of the latter two compounds used. Generally, however, the microcapsules of compact and complete wall structure having no substantial tendency to cause agglomeration of each capsules are prepared by using the phospholipids at a ratio of about 0.0002 to about one gram, especially 0.0006 to 0.3 gram, to one gram of the total amount of ethylcellulose and the pharmaceutically active compound to be used. Further, the amount of ethylcellulose to be used may be varied within the range of about 0.02 to about 5 gram per gram of the pharmaceutically active compound, and the wall thickness of the microcapsules can be readily adjusted by changing the quantitative ratio of said ethyl-cellulose to the pharamceutically active compound within the above range.

In making the ethylcellulose microcapsules of the pharmaceutically active compound in accordance with the present invention, it is preferred to dissolve ethylcellulose and the phospholipids in cyclohexane at about 75° to about 80° C., and then dispersing thereto the pharmaceutically active compound. It is also preferred that the phospholipids and ethylcelulose are dissolved in cyclohexane at concentrations of about 0.01 to about 10 w/v % and about 0.5 to about 10 w/v %, respectively. When the above-obtained dispersion is then cooled gradually (e.g., at a rate of 0.05° to 5° C., especially about 0.4° C., per minute) under continuous stirring at about 20 to about 600 rpm, ethylcellulose in the form of "gel" separates out from the dispersion at about 68° C. mainly by flocculation thereof depositing on or wrapping the prticles of the pharmaceutically active compound, and the ethylcellulose gel thus deposited forms seamless and complete walls at about 50° C. When the temperature is further lowered to a temperature not higher than 50° C. (e.g., 20° to 50 ° C.), the thus-formed embryonic capsules are shrunken and become solid by solvent loss from the capsule walls, thus giving the pharmaceutically active compound-containing microcapsules. The microcapsules thus obtained may be recovered by conventional manners such as, for example, decantation, centrifugation, filtration and so forth. Further, the ethylcellulose microcapsules of a pharmaceutically active compound which are substantially free from the phospholipids can be readily obtained by washing the thus-obtained microcapsules with cyclohexane, petroleum ether, n-hexane and so forth, i.e., with an organic solvent which dissolves phospholipids but does not dissolve both of ethylcellulose and the pharmaceutically active compound used.

In the above-mentioned method of the present invention, the phospholipids used as the phase-separation-inducing agent serves to increase the affinity of ethylcellulose to cyclohexane and thereby improve the visco-elasticity or flexibility of the ethylcellulose gel which separates out during the microencapsulation step. Such increased visco-elasticity of the ethylcellulose gel serves of course to improve the wall characteristics of the ethylcellulose gel deposited on particles of the pharmaceutically active compound, i.e., to form the microcapsules of compact and complete wall structure. Moreover, according to the present invention, the microcapsules of uniform particle size which as such can be used as granules or pulvers are obtained in a high yield because, during the cooling step, each embryonic capsules formed are protected with the adsorption layer of the phospholipids formed on the surface of said capsules thereby keeping them from agglomerating together into small lumps each containing a myriad of individual capsules. In addition, the ethylcellulose microcapsules of a pharmaceutically active compound prepared in the invention have excellent free-flowing characteristics and show no substantial agglomeration of each capsules. Thus, pharmaceutical preparations such as tablets can be prepared therefrom without deterioration in the quality of such preparations (e.g., sticking or capping in compressed tablets). Further, since the phase separation-coacervation or the flocculation of ethylcellulose in the present invention is effected with the aid of the phospholipids i.e., without using an adhesive polymer material as the phase-separation-inducing agent, the pharmaceutically active compound-containing microcapsules substantially free from the solvent and phase-separation-inducing agent are readily obtained by simple washing with cyclohexane or other suitable solvent, followed by drying thereof.

Practical and presently-preferred embodiments of the present invention are illustratively shown in the following lines.

EXPERIMENT I

To compare the effect of phase-separation-inducing agents in making microcapsules, ethylcellulose microcapsules of 1-(3,4,5-trimethoxybenzoyloxy)-2-dimethylamino-2-phenylbutane maleate were prepared as follows:

A phase-separation-inducing agent was dissolved in 300 ml of cyclohexane, and 6 g of ethylcellulose (said ethylcellulose has the ethoxy content of 48.0%, and a 5 w/w % solution thereof in toluene-ethanol(4:1) has the viscosity of 100 cps at 25° C.) were dissolved therein at 78° C. 30 g of 1-(3,4,5-trimethoxybenzoyloxy)-2-dimethylamino-2-phenylbutane maleate (powder) having a particle size of 74 to 149µ were dispersed in the solution, and the dispersion was cooled to room temperature under stirring at 400 rpm. The microcapsules thus formed were recovered by filtration, washed with cyclohexane and dried, whereby about 34 g of the active ingredientcontaining microcapsules (Microcapsule "A") were obtained. Said microcapsules were then passed through the nest of JIS (=JAPANESE INDUSTRIAL STANDARD) standard sieve (350µ aperture) to obtain microcapsules (Microcapsule "B") which met the requirements of "Pulvers" specified in THE PHARMACOPOEIA OF JAPAN 9th-Edition. Each characteristics of the microcapsules (Microcapsule "B") thus obtained are shown in Table 1.

TABLE 1

| | Phase-separation-inducing agent and amount (grams) used | | | | | | |
|---|---|---|---|---|---|---|---|
| | (the method of the present invention) | | | | | (control) | |
| | Soybean phospholipids | | | | | butyl rubber | |
| | 0.03g | 0.18g | 0.3g | 3g | 6g | — | 6g |
| Yield of microcapsules (%)* | 87.3 | 90.5 | 96.6 | 97.5 | 99.1 | 33.9 | 96.4 |
| Angle of Repose | 38° | 35° | 30° | 34° | 32° | 54° | 33° |
| Amount of active ingredient (%)** | 86.5 | 85.7 | 85.6 | 85.4 | 85.0 | 89.6 | 90.3 |
| Amount of cyclohexane remained in microcapsules (μg/g) | 4.8 | 0.8 | 0.6 | 2.4 | 1.3 | 0.7 | 97 |
| Taste of microcapsules*** | (−) | (−) | (−) | (−) | (−) | (+) | (−) |

Note:
*Yield of microcapsules was calculated according to the following formula:
$$\frac{\text{Amount of Microcapsule ``B'' obtained}}{\text{Amount of Microcapsule ``A'' obtained}} \times 100$$
**Amount of 1-(3,4,5-trimethoxybenzyloxy)-2-dimethylamino-2-phenylbutane maleate contained in Microcapsule "B".
***(+): bitter taste
(−): tasteless It can be seen from Table 1 that in the method of the present invention the microcapsules suitable for use as pulvers could be obtained in a high yield, and said microcapsules of the invention showed better free-flowing property as compared with those prepared in the absence of a phase-separation-inducing agent.

EXPERIMENT II 3 g of egg yolk phospholipids were dissolved in 300 ml of cyclohexane, and ethylcellulose (said ethylcellulose has the ethoxy content of 48.0 w/w %, and a 5 w/w % solution thereof in toluene-ethanol (4:1) has the viscosity of 100 cps at 25° C.) was dissolved therein at 78° C. 30 g of calcium N-(γ,γ-dihydroxy-β,β-dimethylbutyryl)-γ-aminobutyrate having a particle size of 74 to 177 were dispersed in the solution, and the dispersion was cooled to room temperature under stirring at 300 rpm. The microcapsules thus formed were recovered by filtration, washed with cyclohexane and dried, whereby about 31 to 38 g of the active ingredient-containing microcapsules (Microcapsule "A") were obtained. Said microcapsules were then passed through the nest of JIS standard sieve (350μ aperture) to obtain microcapsules (Microcapsule "B") which met the requirements of "Pulvers" specified in THE PHARMACEOPIEIA OF JAPAN 9th-Edition. The characteristics of the microcapsules (Microcapsule "B") thus obtained are shown in Table 2. It can be seen from this table that the coating thickness of the microcapsules of the invention can be increased in parallel with increase in the quantity of ethylcellulose used.

TABLE 2

| | Wall-forming material and amount (grams) used Ethylcellulose | | |
|---|---|---|---|
| | 3.3g | 7.5g | 12.9g |
| Yield of microcapsules (%)* | 95.3 | 98.7 | 97.4 |
| Angle of Repose | 34° | 33° | 38° |
| Amount of active ingredient (%)** | 92.4 | 83.9 | 75.4 |
| Amount of cyclohexane remained in microcapsules (g/g) | 1.4 | 1.8 | 2.1 |
| Taste of microcapsules*** | (±) | (−) | (−) |

Note:
*same as defined in the footnote of Table 1.
**amount of calcium N—(γ,γ-dihydroxy-β,β-dimethylbutyryl)-γ-aminobutyrate contained in Microcapsule "B".
***(+): slightly bitter taste
(±): slightly bitter taste
(−): tasteless

EXAMPLE 1

0.3 g of soybean phospholipids was dissolved in 300 ml of cyclohexane, and 4 g of ethylcellulose (said ethylcellulose has the ethoxy content of 48.5 w/w %, and a 5 w/w % solution thereof in toluene-ethanol (4:1) has the viscosity of 100 cps at 25° C.) were dissolved therein at 78° C. 30 g of glutathione having the particle size of 105 to 250μ were dispersed in the solution, and the dispersion was cooled to room temperature under stirring at 400 rpm. The microcapsules thus formed were recovered by decantation, washed with petroleum ether and dried, whereby 34 g of the glutathione-containing microcapsules were obtained. Said microcapsules were then passed through the nest of JIS standard sieves (500 and 105μ apertures), and 32.4 g of microcapsules having the particle size of 105–500μ which met the requirements of "Fine Granules" specified in THE PHARMACOPOEIA OF JAPAN 9th-Edition were collected therefrom. Yield (calculated in the same manner as described in Table 1): 95.3%

The characteristics of the microcapsules thus obtained are shown as follows:
Angle of repose: 28°
Amount of glutathione contained in the microcapsules: 90.8%
Amount of cyclohexane remained in the microcapsules: 0.5 g/g
Amount of petroleum ether remained in the microcapsules: 0.1 g/g To compare the glutathione-containing microcapsules with powdery glutathione, a mixture of said microcapsules and sodium bicarbonate (quantitative=1:1) was stored under conditions of a temperature of 30° C. and a relative humidity of 92% for 11 days. As a result, the glutathione-containing microcapsules of the invention showed neither discoloration nor hygroscopicity, whereas a mixture of powdery glutathione and sodium bicarbonate (quantitative ratio=1:1) stored under the same conditions as above was discolored to pale yellow and formed cohesive mass by absorbing about 18% of water.

EXPERIMENT 2

3 g of phosphatidyl choline, 4 g of ethylcellulose (said ethylcellulose has the ethoxy content of 48.5 w/w %, and a 5 w/w % solution thereof in toluene-ethanol (4:1) has the viscosity of 100 cps at 25° C.) and powdery di-(2-thiethyl)-(N-methyl-5-methoxy-3-piperidylidene)methane methylbromide (said piperidylidene methane was passed through the nest of JIS standard sieve (149μ aperture) beforehand) were treated in the same manner as described in Example 1. The microcapsules thus formed were recovered by decantation, washed with petroleum ether and dried, whereby 34 g of the di-(2-thienyl)-(N-methyl-5-methoxy-3-piperidylidene)methane methylbromide-containing microcapsules were obtained. Said microcapsules were then passed through the nest of JIS standard sieve (350μ aperture), and 32.8 g of microcapsules which met the requirements of "Pulvers" specified in THE PHARMACOPOEIA OF JAPAN 9th-Edition were collected therefrom. Yield (calculated in the same manner as described in Table 1):96.6%

The characteristics of the microcapsules thus obtained are shown as follows:
Angle of repose: b 31°
Amount of di(2-thienyl)-(N-methyl-5-methoxy-3-piperidylidene)methane methylbromide contained in the microcapsules: 87.8%
Amount of cyclohexane remained in the microcapsules: 0.9μ g/g
Amount of petroleum ether remained in the microcapsules: 0.1μ g/g The thus-obtained ethylcellulose microcapsules (85 w/w %) containing di-(2-thienyl)-(N-methyl-5-methoxy-3-piperidylidene)-methane methylbromide was mixed with lactose (10 w/w %), corn starch (3.5 w/w %) and magnesium stearate (1.5 w/w %). This mixture could be compressed successively into tablets (each tablet having the hardness of 9 kg and the weight of 200 mg) without capping or sticking of said compressed tablets. However, when the powder of di-(2-thiethyl)-(N-methyl-5-methoxy-3-piperidylidene)methane methylbromide was used instead of the microcapsules obtained above, it was difficult to prepare the corresponding compressed tablets because of high incidence of capping and sticking of resultant tablets.

EXAMPLE 3

1.5 g of phosphatidyl ethanolamine, 4 g of ethylcellulose (said ethylcellulose has the ethoxy content of 48.5 w/w %, and a 5% solution thereof in toluene-ethanol (4:1) has the viscosity of 100 cps at 25° C.) and 20 g of powdery vitamine C having the particle size of 74–105μ were treated in the same manner as described in Example 1. The microcapsules thus formed were recovered by decantation, washed with petroleum ether and dried, whereby 24 g of the vitamine C-containing microcapsules were obtained. Said microcapsules were then passed through the nest of JIS standard sieve (350μ aperture), and 21.9 g of microcapsules which met the requirements of "Pulvers" specified in THE PHARMACOPOEIA OF JAPAN 9th-Edition were collected therefrom. Yield (calculated in the same manner as described in Table 1): 91.3%

The characteristics of the microcapsules thus obtained are shown as follows:
Angle of repose: 34°
Vitamine C content in the microcapsules: 85.1 %
Amount of cyclohexane remained in the microcapsules: 0.75μ g/g
Amount of petroleum ether remained in the microcapsules: 0.1μ g/g A mixture of said vitamine C-containing microcapsules, O-benzoylthiamine disulfide and lactose (quantitative ratio=2:1:4) was stored under conditions of a temperature of 40° and a relative humidity of 75% for 7 days. As a results, the vitamine C-containing microcapsules showed no discoloration, whereas a mixture of powdery vitamine C, O-benzoylthiamine disulfide and lactose (quantitative ratio=2:1:4) stored under the same conditions as above was discolored to brown.

What we claim is:
1. A process for preparing microcapsules containing a pharmaceutically active compound comprising: dissolving
   (a) about 0.02 to about 5 g per gram of said compound of ethylcellulose, and
   (b) about 0.0002 to about 1 g per gram of the total of said ethylcellulose plus said compound of phospholipids
in cyclohexane, dispersing articles of the compound in said solution, cooling the dispersion under continuous stirring until the ethylcellulose separates out from the dispersion, thereby coating the particles of compound, and then recovering the microcapsules formed.

2. The process according to claim 1, wherein ethylcellulose having an ethoxy content of about 47.0 to about 51.0 w/w % is used.

3. The process according to claim 1 wherein the phospholipids are selected from the group consisting of soybean phospholipids, egg-yolk phospholipids, phosphatidyl cholin and phosphatidyl ethanolamine.

4. The process according to claim 2, 3, or 1 wherein the ethylcellulose and phospholipids are dissolved in cyclohexane at a temperature of about 75° to about 80° C., and the dispersion containing said pharmaceutically active compound is cooled gradually to a temperature not higher than 50° C. under conditions stirring at about 20 to about 600 rpm.

5. The process according to claim 4, wherein said dispersion is cooled at a rate of 0.05° to 5° C. per minute.

6. The process according to claim 4, wherein a pharmaceutically active compound having a particle size of not more than 1000μ is used.

7. The process according to claim 4, wherein the phospholipids are dissolved in cyclohexane at a concentration of about 0.01 to about 10 w/w %, and the ethylcellulose is dissolved therein at a concentration of about 0.5 to about 10 w/w %.

* * * * *

UNITED STATES PATENT AND TRADEMARK OFFICE
CERTIFICATE OF CORRECTION

PATENT NO. : 4,389,331
DATED : June 21, 1983
INVENTOR(S) : SAMEJIMA, et al

It is certified that error appears in the above—identified patent and that said Letters Patent are hereby corrected as shown below:

Column 3, line 8, correct "formalin"
Column 3, line 35, correct "ethylcellulose"
Column 3, line 43, after "thereof" insert --thereby--
Column 3, line 44, correct "particles"
Column 4, line 59, correct "ingredient-containing"

IN THE CLAIMS

Column 8, line 26, correct "particles"
Column 8, line 54, change "10 w/w%" to -- 10 w/v% --

Signed and Sealed this

Twenty-seventh Day of November 1984

[SEAL]

Attest:

GERALD J. MOSSINGHOFF

Attesting Officer

Commissioner of Patents and Trademarks